(12) United States Patent
Rytky et al.

(10) Patent No.: US 8,467,861 B2
(45) Date of Patent: Jun. 18, 2013

(54) ACCESSORY FOR PERFORMANCE-MONITORING DEVICE

(75) Inventors: Pekka Rytky, Oulu (FI); Olli Kokkoneva, Oulu (FI)

(73) Assignee: Polar Electro Oy, Kempele (FI)

( * ) Notice: Subject to any disclaimer, the term of this patent is extended or adjusted under 35 U.S.C. 154(b) by 195 days.

(21) Appl. No.: 12/428,777

(22) Filed: Apr. 23, 2009

(65) Prior Publication Data

US 2010/0106034 A1    Apr. 29, 2010

(30) Foreign Application Priority Data

Apr. 29, 2008 (FI) .................................. 20085384

(51) Int. Cl.
*A61B 5/04* (2006.01)

(52) U.S. Cl.
USPC ........................................................ 600/509

(58) Field of Classification Search
USPC .................................. 600/509, 382, 386–390
See application file for complete search history.

(56) References Cited

U.S. PATENT DOCUMENTS

| | | | |
|---|---|---|---|
| 4,120,294 A | | 10/1978 | Wolfe |
| 4,809,700 A | * | 3/1989 | Castelli .......................... 600/384 |
| 5,203,344 A | * | 4/1993 | Scheltinga et al. ............ 600/547 |
| 5,226,425 A | | 7/1993 | Righter |
| 7,330,751 B2 | * | 2/2008 | Ueda .............................. 600/509 |
| 2002/0026114 A1 | | 2/2002 | Nissila |
| 2003/0040305 A1 | * | 2/2003 | Ng et al. ........................ 455/419 |
| 2004/0019288 A1 | * | 1/2004 | Kinast .............................. 600/509 |
| 2004/0220485 A1 | * | 11/2004 | Rytky ............................. 600/509 |
| 2007/0179376 A1 | * | 8/2007 | Gerder ........................... 600/393 |

FOREIGN PATENT DOCUMENTS

| | | |
|---|---|---|
| EP | 1186272 A1 | 3/2002 |
| EP | 1468645 A1 | 10/2004 |
| WO | WO0178594 A1 | 10/2001 |
| WO | WO 2004045405 A1 * | 6/2004 |
| WO | WO2004045405 A1 | 6/2004 |

OTHER PUBLICATIONS

S. Mundakapadam, European Office Action for corresponding European Application No. 09 158 814.5, p. 1-4 (Nov. 25, 2010).

* cited by examiner

*Primary Examiner* — Christopher D Koharski
*Assistant Examiner* — Nadia Ahmad
(74) *Attorney, Agent, or Firm* — Hoffmann & Baron, LLP

(57) ABSTRACT

There is provided an electric apparatus for monitoring an electrocardiogram signal of a person, comprising an attaching mechanism configured to enable the attachment of the electric apparatus to a wearable item, first and second electrodes for electrical contact with the skin of the person, wherein, during operation, the first electrode is placed between the wearable item and the skin of the person and the second electrode is placed on the opposite side of the wearable item, a detector configured to detect the electrocardiogram signal between the two electrodes, and a transmitter configured to transmit wirelessly information regarding the electrocardiogram signal detected by the detector.

18 Claims, 2 Drawing Sheets

ACCESSORY FOR PERFORMANCE-MONITORING DEVICE

CROSS-REFERENCE TO RELATED APPLICATION

This application claims priority based on Finnish Patent Application No. 20085384, filed Apr. 29, 2008, which is incorporated herein by reference.

BACKGROUND

1. Field

The invention relates to an accessory device for a performance-monitoring device, wherein the performance monitoring relates to measuring heart rate information non-invasively.

2. Description of the Related Art

Nowadays people are increasingly concerned about their own health and physical endurance. One way to ease the concern is to provide means for monitoring heart rate non-invasively with a device or system designed for that purpose. The monitoring can be performed during physical exercise or it can be done, for example, while watching a TV-program.

An exemplary system designed for that purpose includes a transmitter and a receiver, wherein the transmitter is typically a belt worn around the chest of a user, and the receiver can be, for example, a wrist computer. A detector in the transmitter detects the heart rate of the person and transmits information to the receiver that is capable of processing the received information and displaying it to the user.

Heart rate can be measured from an electrocardiogram (ECG) signal of the user. The ECG signal is an electromagnetic signal generated by the heartbeat of a human and detectable on the skin of the human. Generally, the belt worn by the user comprises two electrodes that are in electrical contact with the skin of the user in order to measure the electromagnetic ECG signal. The detector of the belt is able to detect the potential difference between the two electrodes. From this information, the processor of the transmitter/receiver may generate heart rate information and display it to the user via a display.

The usability of the belt as a transmitter is not an ideal solution. It takes time to put on the belt around the chest, and the belt may the belt may cause discomfort. On the other hand, if the belt is too loose the electric contact between the electrode and the skin is not sufficient for reliable ECG detection. The ability to instantly check the heart rate by using the belt as an ECG detector requires that the belt is worn. Therefore, the belt should be at least carried with the user all the time so that the user can put it on when desired. Thus, a more practical solution for instantly checking the heart rate is needed.

SUMMARY

An object of the invention is to provide an electric apparatus for monitoring and measuring the ECG signal of the user of the apparatus.

According to an aspect of the invention, there is provided an apparatus as specified in claim 1.

Embodiments of the invention are defined in the dependent claims.

BRIEF DESCRIPTION OF THE DRAWINGS

In the following, the invention will be described in greater detail with reference to the embodiments and the accompanying drawings, in which.

DETAILED DESCRIPTION

The following embodiments are exemplary. Although the specification may refer to "an", "one", or "some" embodiment(s) in several locations, this does not necessarily mean that each reference is made to the same embodiment(s), or that a particular feature only applies to a single embodiment. Single features of different embodiments may also be combined to provide other embodiments.

Because the belt, or any ECG signal detector that is carried with the user separately in a pocket or in a bag, for example, is not the ideal solution with respect to user friendliness, an embodiment of the present invention provides an electric apparatus that may be attached to an item that a person wears and, thus, carried with the person constantly. Further, as the apparatus is attached to the wearable item, it may simultaneously be in operating condition. Accordingly, it is possible to check the heart rate of the user instantly without putting on any belts or similar conventional ECG signal detectors. A detailed description of the apparatus will be given in the following.

Figure 1:
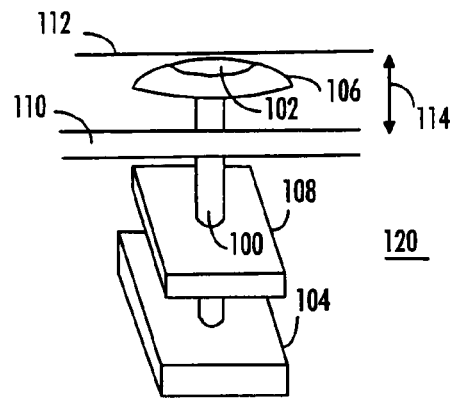
FIG. 1 presents a perspective view of an electric apparatus according to an embodiment.

FIG. 1 presents a perspective view of an electric apparatus 120 according to an embodiment. The electric apparatus 120 may comprise an attaching mechanism 100 that may enable an attachment of the electric apparatus 120 to the wearable item 110. The attaching mechanism 100 may further be an integral part of the electric apparatus 120. The wearable item 110 may be, for example, a wristband of a wrist device such as sport watch, a shirt, a sock, a cufflink or a sweatband. The attaching mechanism 100 may enable the attachment of the electric device to a plurality of wearable items. The wearable item 110 may comprise several layers or it may be a single-layer wearable item.

Further, according to an embodiment, the attaching mechanism 100 may enable the detachment of the electric apparatus 120 from the wearable item 110. Thus, the electric apparatus 120 may be, for example, switched to another wearable item if needed.

FIG. 1 further shows a first electrode 102 and a second electrode 104. The wearable item 110 forms a planar structure having two sides: a first side facing the skin 112 of the person and a second side being opposite to the first side. The second side may face outer clothing layers or it may form the outmost clothing surface. The second side is also called as an opposite side of the wearable item.

During operation, the first electrode 102 is placed between the wearable item 110 and the skin 112 of the person and the second electrode 104 is placed on the opposite side of the wearable item 110. The second electrode 104 provides the apparatus 120 with an electrical contact with the skin 112 of the person during the use of the electric apparatus 120.

An electrode 102, 104 may comprise a plurality of sub-electrodes. Thus, a term "electrode" may be replaced with the term "electrode structure", wherein the electrode structure may comprise several electrodes or sub-electrodes.

One of the two electrodes 102, 104 may be in an electrical contact with the skin of a hand and the other electrode 102, 104 may be in electrical contact with the skin of a body part other than the hand that is in electrical contact with the other electrode 102, 104. The electrode having a contact with the skin of the hand may be the first electrode 102 or the second electrode 104. Similarly, the electrode that is in electrical contact with the skin of a body part other than the hand may be either the first electrode 102 or the second electrode 104. This way one of the two electrodes 102, 104 may always be in contact with the skin and another electrode 102, 104 may be in a position that allows external access to the electrode. That is, the electrode 102, 104 can be pressed with a hand, leg, head, neck, or torso of the person wearing the electrode 102, 104.

Further, the electrodes 102 and 104 may be electrically separated so that current flow between the two electrodes 102 and 104 may occur, during operation, only via the skin of the person 112.

The first electrode 102 may be mounted on a flexible base 106 with adaptable thickness on the basis of the space 114 between the wearable item 110 and the skin of the person 112, thus providing skin-tight contact for the first electrode 102. For example, if the electric apparatus 120 is attached to a wristband of a wrist device, the space 114 between the wristband and the skin may vary depending on the position of the palm of the hand with respect to the wrist, the tightness of the wristband and the opening direction of the palm of the hand. Thus, as the first electrode 102 may be mounted on the base 106 with flexible thickness, the skin contact between the first electrode 102 and the skin may always be skin-tight.

In an embodiment of the invention, the second electrode 104 is integrated into the cover of the electric apparatus 120, which enables a large surface area of the second electrode 104 being implemented, thus providing easy external access to the second electrode 104. This is especially beneficial if the size of the electric apparatus 120 is in the order of centimeters.

Figure 6:
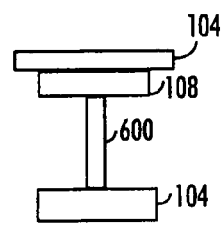
FIG. 6 presents an attaching mechanism according to an embodiment.

With reference to FIG. 6, the attaching mechanism may comprise a rod that may be extended through a hole of the wristband. The rod 600 may work as an attaching mechanism and it may be extended through a buttonhole of a shirt or a hole in the wristband of a wrist device. The two electrodes 102 and 104 may be used to measure the ECG signal. FIG. 6 also presents a detector 108, which will be explained later in detail.

Figure 7:
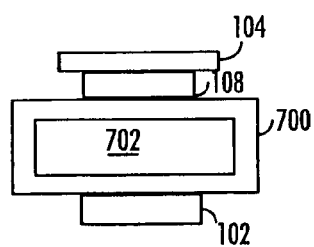
FIG. 7 presents an attaching mechanism according to an embodiment.

With reference to FIG. 7, the attaching mechanism 700 may be in the form of a ring, ellipse or square with a hole in the middle in order to allow, for example, the wristband of the wrist device to be passed through a hole 702 and thereby allowing the attachment of the electrical apparatus to the wristband. The electrodes 102 and 104 are placed on both sides of the attaching mechanism 700. As in FIG. 6, the detector 108 is also shown here.

The electric apparatus 120 may also comprise a detector 108, (see FIG. 1). The detector 108 may be applied to detect the electrocardiogram signal between the two electrodes 102 and 104.

The detector 108 may further detect whether or not the skin of a person 112 is in contact with both of the electrodes 102 and 104. This may be performed by, for example, feeding a small electric current in the order of 50 nanoamperes to the electrodes 102, 104 and measuring the impedance between the electrodes 102 and 104. Because the only galvanic contact between the electrodes is via the skin of a person 112, both electrodes 102 and 104 need to be in touch with the skin of the person 112 for the detector 108 to observe relatively low impedance values in the order of one MΩ between the electrodes 102 and 104. When either of the electrodes 102 and 104 is not in touch with the skin of a person 112, the impedance is significantly larger.

Alternatively, the detection of the skin of a person 112 against the electrodes 102 and 104 may be performed with pressure sensitive layers on top of the electrodes 102, 104. This way the detector 108 may observe when enough pressure is applied against the electrodes 102 and 104.

Further, the electric apparatus 120 may comprise, for example, a button for turning the detector 108 off, thus saving the battery life of the electric apparatus 120. The same button may be used to turn the detector 108 on.

Figure 2A:
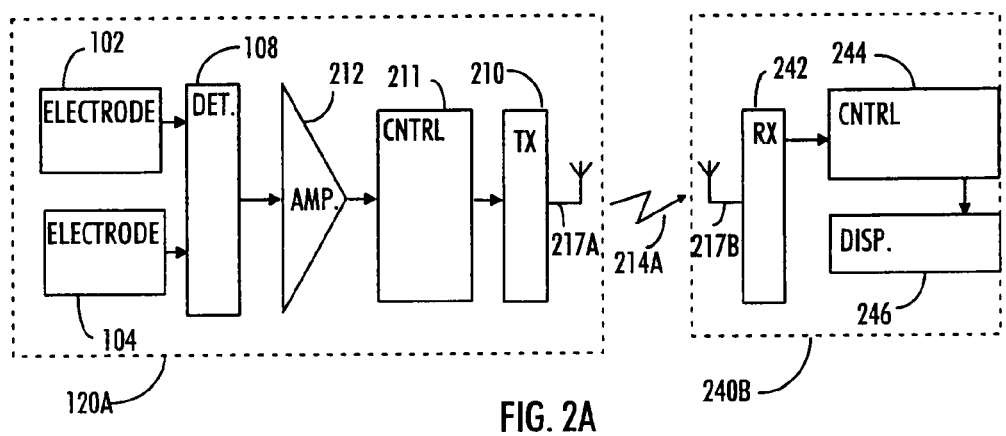
FIG. 2A shows a block diagram of a receiver and -electric apparatus according to an embodiment.
Figure 2B:
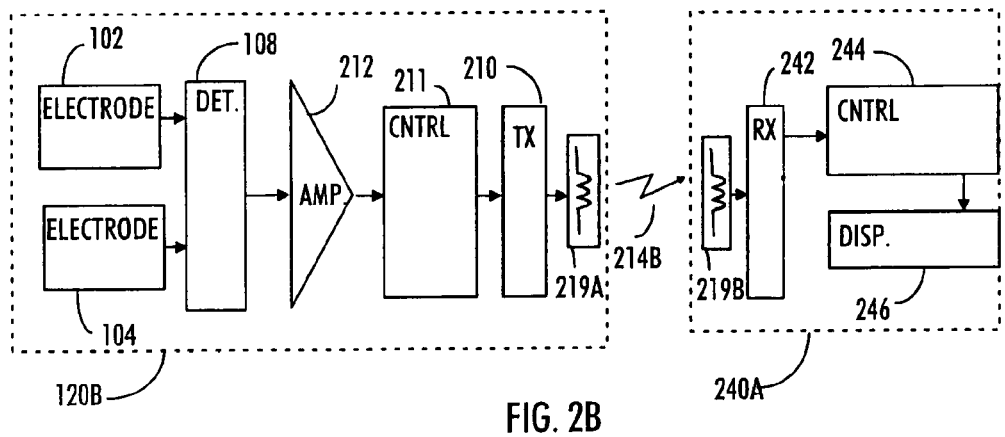
FIG. 2B shows a block diagram of a receiver and electric apparatus according to an embodiment.

FIG. 2A and FIG. 2B represent block diagrams of the electric apparatuses 120A, 120B and the receiver apparatuses 240A, 240B according to two embodiments of the invention. The embodiment in FIGS. A and B are otherwise identical, except that they differ in the way information is transmitted to the receiver apparatus 240A, 240B. The electric apparatus 120A, 120B may comprise the two electrodes 102 and 104, the detector 108 and a transmitter 210. Even though both of the electrodes 102 and 104 are connected to the detector 108, the electrodes 102 and 104 are electrically separated, i.e., the only galvanic connection between the electrodes 102, 104 is via the skin of a person 112 although this is not shown in the figures.

The electric apparatus 120A, 120B may further comprise an amplifier 212 which amplifies the electrocardiogram signal detected between the two electrodes 102, 104, wherein at least one of the electrodes 102 and 104 is in contact with the skin of a hand. The output of the amplifier 212 may be fed as input to the transmitter 210 or to a processor 211.

The electric apparatus 120A, 120B may further comprise the transmitter 210 which may be configured to transmit wirelessly information regarding the electrocardiogram signal detected by the detector 108. A receiver apparatus 240A, 240B for the transmitted information may be, for example, a computer or a wrist device such as wrist computer produced by Polar™. The transmitter 210 may start the wireless transmission when the detector 108 has detected that both of the electrodes 102 and 104 are in contact with the skin.

The transmitter 210 may transmit information regarding the electrocardiogram signal wirelessly 214A, 214B during operation. The information may be transmitted in a radio frequency signal through antennas 217A and 217B as is the case in FIG. 2A. For example, the radio frequency transmission 214A may utilize the Bluetooth® standard, or any other suitable standard/non-standard wireless communication methods utilizing electric and/or magnetic fields. An exemplary frequency for this type of transmission is 2.4 GHz, for instance. The transmitter 210 may, thus, comprise an antenna for accessing the radio interface.

Alternatively, the transmission 214A, 214B may be performed via magnetic pulses that are transmitted through a coil 219A on the transmitter 210 side and received by another coil 219B on the receiver 242 side. An exemplary frequency for this type of transmission 214B is 5.5 kHz, for instance. in this case the information regarding the electrocardiogram signal may typically comprise one pulse transmitted to the receiver apparatus 240B for each heartbeat detected from the electrocardiogram signal in order to allow the receiver apparatus 240B to generate information regarding the heart rate of the person.

In an embodiment of the invention, the electric apparatus 120A, 120B may comprise a processor 211 that is programmed to receive information regarding the electrocardiogram signal from the detector 108 and to generate, from the received electrocardiogram signal, information regarding the heart rate of the person, wherein the information regarding the heart rate of the person is transmitted to the receiver apparatus 240A, 240B. The processor 211 is, however, not necessarily needed. The processor 211 may, for example, estimate the time of the heartbeat on the basis of the ECG signal, and generate an estimate for the heart rate from the estimated heartbeat times. Further, the processor 211 may generate other type of information, such as the variance of the heart rate and the upper and lower limits. The processor 211 may comprise a memory for storing heart rate information in order to generate statistical parameters, such as the average heart rate. The processor 211 may be implemented with a digital signal processor provided with suitable software embedded on a computer readable medium, or with separate logic circuits, for example with an application-specific integrated circuit (ASIC).

Thus, the output of the processor 211 may be for example a data structure comprising the measured heart rate information. The data structure may be coded or uncoded. That is, the processor 211 may perform coding procedures before outputting the signal towards the transmitter 210 in order to improve the reliability of the wireless transmission 214A, 214B. Consequently, the receiver apparatus 240A, 240B, when receiving the information, may not need to process the information before displaying it to the user.

Further, the information regarding the electrocardiogram signal from the electric apparatus 120A, 120B may comprise an identifier for identifying the electric apparatus 120A, 120B. The identifier may be, for example, a header bit in the transmitted data in order to add an apparatus-specific code in to the transmitted information.

The electric apparatus 120A, 120B may also comprise, although not shown in the figure, a power source for providing power to enable the detection, processing and transmission.

The receiver apparatus 240A, 240B may comprise a receiver 242 which receives the wireless transmission 214A, 214B via the antenna 217B or the coil 219B, respectively, and outputs the received information to a processor 244. The processor 244 may, for example, process the received information and generate heart rate information. However, if there is a processor present already in the electric apparatus 120A, 120B and the processor has performed estimations of the heart rate information already at the electrical apparatus 120A, 120B, the processor 244 in the receiver apparatus 240A, 240B might not have to perform any calculations and estimations of the heart rate-related information on the received signal. The heart rate information may be displayed to the user with a display 246. The display 246 may be a liquid crystal display or a similar viewing instrument.

Figure 3:
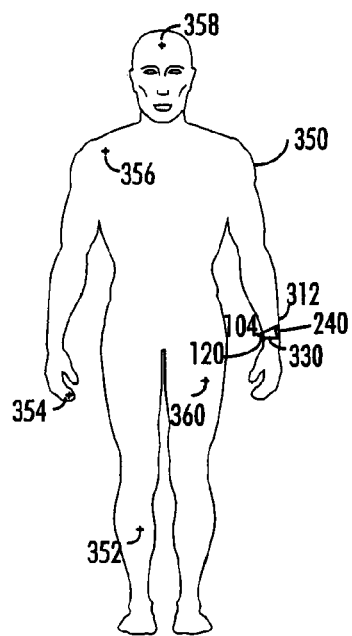
FIG. 3 illustrates a human wearing an electric apparatus according to an embodiment.

FIG. 3 illustrates a human wearing the electric apparatus 120 according to an embodiment. In this embodiment, the electric apparatus 120 is attached to a wristband 330 of the receiver apparatus 240. The wearable item 110 may, thus, be the receiver apparatus 240 including the wristband 330. That is, the first electrode 102 of the electrical apparatus 120, although not shown in FIG. 3, may be placed between the wristband 330 and the skin of the wrist 312. The second electrode 104 may be placed on the opposite side of the wearable item 110, thus providing easy external access to the second electrode 104.

Hence, for the embodiment shown in FIG. 3, the first electrode 102 is the one having the electrical contact with the skin of the hand and placed between the wristband 330 and the skin of the wrist 312, while the second electrode 104 may be in electrical contact with another body part. The attaching mechanism shown in FIGS. 6 and 7 may be suitable for attaching the electric apparatus 120 to the wristband 330.

The skin of a body part other than the hand that is in electrical contact with the first electrode 102 comprises the skin of any of the following: the other hand, the legs and torso including head and neck. FIG. 3 illustrates a few possible body parts with plus-marks 352-360 on the person 350 for providing electrical contact with the second electrode 104. As can be seen, the electrical contact with the second electrode 104 may be obtained with a plurality of body parts. Further, it is not required that, for example, exactly the location of thigh presented with reference number 360 is contacted to the second electrode 104, but the location of the thigh may vary as required by the user 350.

Figure 4:
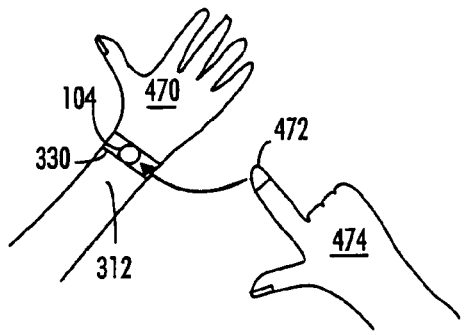
FIG. 4 shows how the ECG signal is monitored according to an embodiment.

FIG. 4 shows how the monitoring of the ECG signal may be performed according to an embodiment. For the embodiment shown in FIG. 4, the first electrode 102, although not shown in the Figure, is the one having the electrical contact with the skin of the hand 470 and placed between the wristband 330 and the skin of the wrist 312, while the second electrode 104 may be attached to the external side of the wristband 330 of the hand 470 with the attaching mechanism of the wristband 330.

The user pressing his/her finger 472 of the other hand 474 against the electrode 104 may trigger the monitoring of the ECG signal by the detector 108. Consequently, the detector 108 may detect the ECG signal and the transmitter 210 may transmit information regarding the ECG signal to the receiver apparatus 240 wirelessly. The detector 108 may detect the moment when the finger 472 is pressed against the second electrode 104 by means of a pressure-sensitive layer on top of the electrode 104 or by means of impedance measurement between the electrodes 102, 104.

Alternatively, the user may bring the electrode 104 into contact with a part of the body other than the finger 472 of the other hand 474 as explained earlier.

When attached to the wristband of a wrist device, the user may instantly measure his/her heart rate information, such as heart rate or heart rate variation by touching the second electrode 104 by hand and check the heart rate information from the wrist device display.

Figure 5:
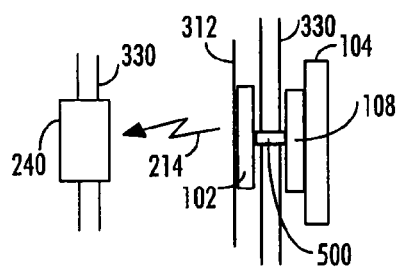
FIG. 5 illustrates the operation of an electric apparatus according to an embodiment.

FIG. 5 illustrates the operation of the electric apparatus 120 according to an embodiment. A receiver apparatus 240 in the form of a wrist device may be capable of receiving information regarding the electrocardiogram signal detected by the detector 108, and a conducting rod 500 may work as the attaching mechanism by enabling the attachment of the electric apparatus 120 to the wristband 330 of the wrist device. Thus, the electric apparatus 120 may be attached with the conducting rod 500 to the wearable item in the form of a wristband 330. The wristband 330 may be part of the receiver 240. The first electrode 102 may be placed between the wristband 330 and the skin of the wrist 312, while the second electrode 104 is on the opposite side of the wristband 330.

This embodiment enables wireless transmission 214 over a short distance. Thus, the transmitter characteristics of the transmitter may be chosen in such a way that the transmission coverage is in the order of five centimeters. This may be very useful in, for example, saving the battery of the transmitter and implementing the transmitter electronics with smaller components.

The attaching mechanism 100 may be an integral part of the electric apparatus 120. It may be, for example, at least partially integrated with one of the electrodes 102 and 104. Thus, referring to FIG. 5, the attaching mechanism may include a conducting rod 500 and a conducting flange, such as the electrode 102, wherein the conducting rod 500 is coupled with the detector 108 and configured to extend through, for example, a hole of the wristband 330 of the wrist device, and the flange is attached to the conducting rod 500 during operation and positioned between the skin of the wrist 312 and the wristband 330, thus providing an electric contact between the conducting rod 500 and the skin of the wrist 312. The detector 108 may also be electrically contacted to the second electrode 104, thus enabling the detector 108 to determine the ECG signal between the flange and the electrode 104.

The detector 108 may be attached to either of the electrodes 102 and 104. Thus, even though the detector 108 is drawn in FIG. 5 to be attached to the second electrode 104, it may as well be directly attached to the first electrode 102.

With reference to FIGS. 2A and 2B, the receiver apparatus 240A, 240B may comprise a plurality of operation modes. In a first operation mode, the receiver apparatus 240A, 240B is configured to continuously record heart rate information. This use case is typical when a conventional chest transmitter, which typically measures the ECG information from the chest, generates the heart rate information. In this case, the receiver apparatus 240A, 240B starts collecting the heart rate information to a file when the receiver apparatus 240A, 240B is set into a recording mode and stops collecting the heart rate information when the receiver apparatus 240A, 240B is set into stop mode.

In a second operation mode, the receiver apparatus 240A, 240B is configured to a discontinuous operation, also called an instant check operation mode, which has benefits when the electric apparatus described in this application is used. In the second operation mode, the receiver apparatus 240A, 240B records the heart rate information only when the receiver 242 receives a detectable signal. The receiver apparatus 240A, 240B may time stamp the heart rate information so that the heart rate information may later be inspected.

Even though the invention is described above with reference to an example according to the accompanying drawings, it is clear that the invention is not restricted thereto but can be modified in several ways within the scope of the appended claims. Further, for a person skilled in the art, it is clear that the described embodiments may, but are not required to, be combined in various ways with other embodiments to further improve the electric apparatus.

The invention claimed is:

1. An electric apparatus for monitoring an electrocardiogram signal of a person, comprising:
   an attaching mechanism configured to attach the electric apparatus to a wrist band of a wrist device capable of wirelessly receiving information regarding the electrocardiogram signal, the attaching mechanism configured to enable detachment of the electric apparatus from the wrist band of the wrist device so that the electric apparatus can be switched to another wrist device;
   first and second electrodes for electrical contact with the skin of the person, the first electrode being configured to be placed between the wrist band of the wrist device and the skin of the person during operation, the second electrode being configured to be placed on the opposite side of the wrist band of the wrist device during operation;
   a detector configured to detect the electrocardiogram signal between the two electrodes, wherein the first and second electrodes form a fixed support structure for the detector; and
   a transmitter configured to wirelessly transmit information regarding the electrocardiogram signal detected by the detector.

2. The apparatus of claim 1, wherein the information regarding the electrocardiogram signal comprises an identifier that identifies the electric apparatus.

3. The apparatus of claim 1, wherein one of the electrodes is at least partially integrated with the attaching mechanism.

4. The apparatus of claim 1, wherein the attaching mechanism includes a conducting rod and a conducting flange, wherein the conducting rod is coupled with the detector and configured to extend through a hole of a wristband of the wrist device, and the flange is attached to the conducting rod during operation and positioned between the skin of the wrist and the wristband, the wristband thus providing an electric contact between the conducting rod and the skin.

5. The apparatus of claim 4, wherein the transmitter characteristics of the transmitter are chosen so that the transmission coverage is in the order of 5 centimeters.

6. The apparatus of claim 1, wherein the first electrode is mounted on a flexible base with adaptable thickness on the basis of the space between the wearable item and the skin of the person, thereby providing skin-tight contact for the first electrode.

7. The apparatus of claim 1, wherein the second electrode is integrated into a cover of the electric apparatus.

8. The apparatus of claim 1, wherein the attaching mechanism includes a hole in the attaching mechanism configured to allow the wristband of the wrist device to be passed through the hole, thereby allowing attachment of the electrical apparatus to the wristband.

9. The apparatus of claim 1, wherein the wireless transmission of information applies magnetic pulses or Bluetooth communication protocol.

10. The apparatus of claim 1, wherein the second electrode is configured to be in contact with a finger and the first electrode is configured to be in contact with a wrist during operation.

11. An electric apparatus for monitoring an electrocardiogram signal of a person, comprising:
    an attaching mechanism configured to attach the electric apparatus to a wrist band of a wrist device capable of wirelessly receiving information regarding the electrocardiogram signal, the attaching mechanism configured to enable detachment of the electric apparatus from the wrist band of the wrist device so that the electric apparatus can be switched to another wrist device;
    first and second electrodes for electrical contact with the skin of the person, the first electrode being configured to be placed between the wrist band of the wrist device and the skin of the person during operation, the second electrode being configured to be placed on the opposite side of the wrist band of the wrist device during operation;
    a detector configured to detect the electrocardiogram signal between the two electrodes; and
    a transmitter configured to wirelessly transmit information regarding the electrocardiogram signal detected by the detector, wherein
    either the attaching mechanism includes a conducting rod, wherein the conducting rod is coupled with the detector and configured to extend through a hole of the wristband of the wrist device, and the first electrode is attached to the conducting rod during operation and positioned between the skin of the wrist and the wristband, thus providing an electric contact between the conducting rod and the skin, or the attaching mechanism includes a hole in the attaching mechanism in order to allow the wristband of the wrist device to be passed through the hole, thereby enabling attachment of the electrical apparatus to the wristband.

12. The apparatus of claim 11, wherein the information regarding the electrocardiogram signal comprises an identifier that identifies the electric apparatus.

13. The apparatus of claim 11, wherein one of the electrodes is at least partially integrated with the attaching mechanism.

14. The apparatus of claim 11, wherein the first electrode is mounted on a flexible base with adaptable thickness on the basis of the space between the wearable item and the skin of the person, thereby providing skin-tight contact for the first electrode.

15. The apparatus of claim 11, wherein the second electrode is integrated into a cover of the electric apparatus.

16. The apparatus of claim 11, wherein the wireless transmission of information applies magnetic pulses or Bluetooth communication protocol.

17. The apparatus of claim 11, wherein the second electrode is configured to be in contact with a finger and the first electrode is configured to be in contact with a wrist during operation.

18. An electric apparatus for monitoring an electrocardiogram signal of a person, comprising:

an attaching mechanism configured to attach the electric apparatus to a wrist band of a wrist device capable of wirelesly receiving information regarding the electrocardiogram signal, the attaching mechanism configured to enable detachment of the electric apparatus from the wrist band of the wrist device so that the electric apparatus can be switched to another wrist device;

first and second electrodes for electrical contact with the skin of the person, the first electrode being configured to be placed between the wrist band of the wrist device and the skin of the person during operation, the second electrode being configured to be placed on the opposite side of the wrist band of the wrist device during operation, wherein the second electrode is integrated into a cover of the electric apparatus;

a detector configured to detect the electrocardiogram signal between the two electrodes; and a transmitter configured to wirelessly transmit information regarding the electrocardiogram signal detected by the detector.

* * * * *